US00PP11096P

United States Patent [19]

Mancebo

[11] Patent Number: Plant 11,096

[45] Date of Patent: Oct. 19, 1999

[54] ALMOND TREE NAMED 'AVALON'

[76] Inventor: Charles Mancebo, 4590 N. Central, Atwater, Calif. 95301

[21] Appl. No.: 08/992,395

[22] Filed: Dec. 17, 1997

[51] Int. Cl.[6] ..... A01H 5/00

[52] U.S. Cl. ..... Plt./155

[58] Field of Search ..... Plt./32.2, 155

*Primary Examiner*—Elizabeth Kemmerer

*Attorney, Agent, or Firm*—Wells, St. John, Roberts, Gregory & Matkin, P.S.

[57] ABSTRACT

A new and distinct variety of almond tree which is somewhat remotely similar to the Nonpareil almond tree (unpatented) but which is distinguished therefrom by producing a crop which is mature for commercial harvesting and shipment approximately 8 days after the Nonpareil variety under the ecological conditions prevailing in Atwater, Calif.

1 Drawing Sheet

BACKGROUND OF THE NEW VARIETY

The present invention relates to a new and distinct variety of almond tree which has been denominated varietarily as "Avalon" and more particularly to such an almond tree which blooms approximately three days earlier in the season than the "Nonpareil", a well-known unpatented almond cultivar, and which further, is mature for commercial harvesting and shipment approximately eight days after the Nonpareil, and six to seven days earlier than the variety "Carmel" (U.S. Plant Pat. No. 2641), under the same environmental conditions prevailing in the San Joaquin Valley of Central California. The subject variety further is distinguished as to novelty by producing crop yields which are equal to, or greater than both the Nonpareil and Carmel varieties under the same environmental conditions.

It has been recognized that it is desirable to provide an almond tree bearing a crop which is ripe for commercial harvesting and shipment in late August and early September and which has the commercially aesthetic appeal such as that presented by the Avalon almond tree. The nut produced by the subject variety of almond tree is noteworthy in that it has a shell which is well sealed, thereby preventing insect damage. Further, it has been discovered that this same variety is a suitable pollinator for both the Nonpareil and Carmel varieties when it is placed in the same orchard.

ORIGIN AND ASEXUAL REPRODUCTION OF THE NEW VARIETY

The present variety of almond tree was discovered as a chance seedling of unknown parentage growing within the cultivated area of the inventor's farm which is located at 4590 N. Central, Atwater, Calif. The inventor noted the novel characteristics of the instant variety of almond tree and marked the chance seedling for subsequent observation.

The first asexual reproduction of the newly discovered variety of almond tree occurred in 1989, when agents of the inventor removed budwood from the chance seedling and budded them into test trees which were then growing on the property of The Burchell Nursery, Inc., located at 12000 Highway 120, Oakdale, Calif. 95361. These same test trees have been continually observed by the inventor and it has subsequently been determined that the budded test trees have identical characteristics to that observed in the original chance seedling.

SUMMARY OF THE NEW VARIETY

The Avalon almond tree is characterized principally as to novelty by producing a consistently good quality nut. The present variety of almond is harvested approximately eight days after the Nonpareil variety of almond tree (unpatented) and six to seven days ahead of the Carmel variety of almond tree (U.S. Plant Pat. No. 2641). As compared to the Nonpareil almond tree, the Avalon almond tree produces a nut that has a shell which is well sealed and thereby impedes insect damage. Still further, the present variety of almond tree is considered average in size and vigor and has a much more upright growth habit when compared to the variety Nonpareil. Yet further, the present newly discovered variety of nut tree has a bloom date which begins earlier in time than the Nonpareil variety of almond tree and overlaps with the bloom time of the Carmel variety almond tree. It being understood that the Carmel almond tree is one of the most widely used pollinators that is planted in plantings of Nonpareil almond trees. Further, the present variety of almond tree is very productive, that is, it produces yields equal to or greater than both the Nonpareil and Carmel almond trees in the orchards which have been observed.

BRIEF DESCRIPTION OF THE DRAWINGS

The accompanying drawing is an illustration by photographic reproduction of a portion of a branch of an almond tree of the new variety showing a mature crop ready for harvesting and shipment; new growth of the present variety showing both the dorsal and ventral coloration of the leaves; and two inset photographs showing the nuts produced by the present variety of almond tree.

DETAILED DESCRIPTION

Referring more particularly to the specific botanical details of this new and distinct variety of almond tree, the following has been observed under the ecological conditions prevailing at The Burchell Nursery, Inc. orchard which is located at 12000 Highway 120, Oakdale, Calif. 95361. All major color code designations are by reference to the Maerz and Paul Dictionary of Color, First Edition, 1930, or alternatively to the ISCC-NBS Color Name Charts. Common color names are also used occasionally.

Tree:

*Generally*.—Size — Medium and upright, depending upon pruning practices. When compared with the Nonpareil variety, the present almond tree is smaller, but has a much more upright growth habit. Density — Considered open. Vigor — Average. Regularity of bearing — Generally — Regular, and occurs predominantly from spurs which are two years old or older. Presently, there is no evidence of bearing on current season shoots, although this trait may depend upon the age and growing conditions of the cultivar being studied. As a general matter, the nuts are distributed throughout the tree.

Trunk:

*Form.*—Generally — Medium as compared with other common almond cultivars.

*Surface texture.*—Average.

Branches:

*Form.*—Average as compared with other common almond cultivars.

*Surface texture.*—Shoots — Relatively slender and smooth.

*Form.*—Straight, and having no current year laterals.

*Length.*—Approximately 6 centimeters to about 27 centimeters (about 3 to about 11 inches).

*Nodes.*—Numbers — Approximately 9 to about 27 nodes will be found.

*Internodes.*—Length — Approximately 1 to 2 centimeters long.

*Shoots.*—Color — Medium green with no reddish flush (26-F-7); (135 l.y.G).

*Buds.*—Position — Terminal, and considered very short and pointed. Further, lateral buds were triangular in shape, pointed, and had dark brown scales with a pubescent margin. Occasionally, double buds may be found at a node.

*Scales.*—Generally — Dark brown, and nondistinctive.

*Spurs.*—Generally — Short and stubby.

*Length.*—Approximately ½ inch or less.

*Numbers.*—2 to 5 lateral buds will normally be found. These will eventually become flower buds.

*Epidermis.*—Color — On spurs which are one year old, the epidermis takes on a green color, but shorter spurs are much darker. This color is not particularly distinctive, however.

*Terminal buds.*—Shape — Pointed, small and very dark. In contrast, lateral buds appear rounded, have a brown color, and a pubescent fringe. This color is not distinctive, however.

*Two year old wood.*—Generally — This wood appears somewhat reddish brown (7-C-8) (58. m. BR.).

*Three year old wood.*—Generally — Many persistent peduncles are present and from which fruit has been borne on previous years. Stem scars are prominent. The color of three year old wood is somewhat lighter brown (57 I BR.) (7-A-7).

*Four year old wood.*—Generally — A dull grayish brown color is evident where the epidermis has sloughed off. This color is not particularly distinctive however. Some spurs continue to produce, but many spurs are clusters of persistent peduncles from earlier production.

Leaves:

*Quantity.*—Abundant.

*Shape.*—Considered long and elliptical, occasionally ovate and tapering to the apex about ⅓ of the way from the apex.

*Tip.*—Shape — Acuminate, and tapering to a more or less acute angle.

*Base angle.*—Obtuse.

*Size.*—Average length — Approximately 25 to 81 millimeters, and having an average length of 59 millimeters.

*Width.*—Approximately 10 to about 25 millimeters, and having an average length of about 16 millimeters.

*Ratio of petiole length to leaf length.*—Approximately 0.25.

*Ratio of blade width to blade length.*—Approximately 0.22.

*Shoot leaves.*—Generally — Medium to large in size, flat and substantially uniform.

*Shoot leave.*—Color — Top surface — (21-D-12) (125 m. OL G). Color — Lower surface — (21-D-10) (118 deep Y G.).

*Marginal form.*—Crenate and having rather shallow crenations.

*Glands.*—Generally — Inconspicuous, or missing.

*Leaf petiol.*—Shape — Grooved and having a mid-rib on the upper side which is quite distinctive.

*Color.*—(18-D-4) (144 1 G).

Flowers:

*Date of first full bloom.*—Approximately Mar. 15, 1997, at the inventor's orchard which is located in Atwater, Calif.

*Bloom.*—Generally — The bloom data was collected from 5 shoots which ranged in length from approximately 10 to about 22 inches. Each shoot additionally had approximately 10 to 24 nodes. The number of nodes bearing flower buds varied from 1 to 7. The total number of flower buds per shoot ranged from approximately 2 to about 13.

*Blossom density.*—Heavy. The blossoms were produced on medium to long shoots as opposed to spurs. In the previous year, the blossoms appeared on short spurs which is probably more typical. The 1997 blossoming pattern was probably a response to lower crop density resulting from the 1996 growing season.

*Flower arrangement.*—Generally — Many double flowers were produced from the same pedicel.

*Bloom time.*—The present variety in comparison to other varieties blooms approximately 3 days ahead of the Nonpareil, and continues in bloom and overlaps with the bloom period of the Carmel almond tree at the same geographical location.

*Pollination compatibility.*—The present variety is a suitable pollinator for both the Nonpareil and Carmel varieties almond tree varieties. Further, the Nonpareil and Carmel have been discovered to be suitable pollinators for the present variety of almond tree.

*Petals.*—Numbers — 5 and occasionally 6 petals may be found.

*Petal overlap.*—The present variety has flowers which are free, that is, the petals are separated from each other in the expanded flower.

*Size of flowers.*—Medium to large, as compared to the flowers of other varieties. Approximately 4 centimeters in diameter at full expansion. Although flowers having a diameter of approximately 3 centimeters may occasionally be found.

*Petals.*—Shape — Broadly obovate and oblong. Each petal has an obtuse tip at the base and a distinctive notch at the apex.

*Petals.*—Marginal edge — Somewhat undulate.

*Petals.*—Length — Approximately 1.8 to about 2 centimeters. A slight crease or vein runs down the approximate center of each petal.

*Flower color.*—Closed buds — Brown to rose pink and deepening in color towards the apex of the bud.

*Sepals color.*—Appear to have a green undercolor which is covered with a reddish rose surface color.

*Opening flowers.*—Colors — Light pink with a deeper pink color present at the apex of the petal. These colors gradually fade to white or very light pink with advancing senescence. A small area of rose pink color is retained at the inside base of each of the petals.

*Stamens*.—Numbers — Approximately 25.

*Pistil*.—Length — Approximately 1.5 centimeters long, and straight. The pistil is pubescent on the lower portion thereof.

*Pistil*.—Position — Extends to near the height of the anther whorl such that the anthers and stigma are approximately at the same level.

Crop:

*Bearing*.—considered regular.

*Harvesting*.—Approximately August 27–September 9. The date of harvesting is considered approximately at the mid-point of the harvesting season as compared to other common varieties. In comparison to the Nonpareil variety of almond tree, the present variety harvests about 8 days after Nonpareil, and approximately 6 to 7 days before the Carmel variety of almond tree at the same geographical location.

*Productivity*.—Considered heavy.

*Distribution of nuts on the tree*.—Well distributed throughout.

*Immature nut*.—Shape — The side view of the immature nut appears round or occasionally oval, and somewhat squarish. Overall, the side view is symmetrical.

*Dorsal edge*.—Generally — Considered evenly sloping, and gently curving from the base to the tip; the immature nut has a small hump that gives it a squarish, flat appearance when viewed from the apical end. Further, the axis from the base to the tip is located very near to the dorsal edge.

*End view*.—Shape — Considered rounded and less symmetrical.

*Base*.—Shape — Appears straight across.

*Apex*.—Shape — Having a small blunt tip having no recurve. Further, the style rudiment is almost missing or only slightly protruding.

*Peduncle attachment*.—Size — A base scar which is considered medium to large and mostly oval and occasionally round in shape, is clearly evident. The immature nut separates cleanly from the peduncle.

*Hull surface*.—Surface texture — Smooth and even.

*Hull surface*.—Color — Olive green — (105 gy g.Y) (18-C-1).

*Surface Texture*.—Generally — A short, fine, fairly abundant pubescence is present. The pubescence gives a whitish to gray tint to the surface which is distributed somewhat unevenly. The surface is further somewhat uneven with grooves and occasionally some depressions or bumps may be found.

*Dehiscence*.— Generally — The dorsal suture is relatively shallow but distinct before dehiscence. The immature nut dehisces on the ventral edge only. This is quite clean and distinct. In many nuts, the hull pulls away with the outer shell still attached.

*Mature nut*.—Generally — Considered a papershell. The outer shell layer tends to separate from the inner shell layer and remains attached to the inside of the hull during dehiscence or is forcefully removed during hulling.

*Size*.—Medium as compared to other varieties. As a general matter, the kernel is darker and plumper than that produced by the Nonpareil variety of almond tree at the same geographical location.

*Shape*.—Side view — Considered round and occasionally oval.

*Ventral edge*.—Shape — Appears gently and uniformly curved from the base to the tip.

*Dorsal edge*.—Shape — Sharply curved, but uniformly so from the base to the tip.

*End view*.— Shape — Slightly oval and considered almost round.

*Wing*.—Generally — A thin and prominent wing extends uniformly from the base to the apex. It is considered fairly wide in relative comparison to other varieties.

*Base scar*.—Shape — Oval and obliquely sloping towards the dorsal edge.

*Apex*.—Shape — Having a sharp acute tip. This acute tip may be knocked off during the hulling process.

*Surface*.—A light brownish tan (12-C-4) (72 d OY).

*Surface texture*.— Relatively smooth but numerous small round dark pits and short grooves appear distributed uniformly over the outer cork.

*Shelling percentage*.—Approximately 64 percent.

*Kernel*.—Length — Approximately 21.6 millimeters.

*Width*.—Approximately 12.7 millimeters.

*Thickness*.—Approximately 9.2 millimeters.

*Kernel*.—The side view of the kernel appears oblong, and obovate and substantially uniformly straight on the dorsal and ventral side. The kernel has a slight taper towards the apex. The base is positioned at a uniformly obtuse angle and further has a somewhat blunt tip. The broadest portion of the kernel is slightly beyond the middle and towards the base.

*Ventral edge*.—Shape — Gradually curving more or less evenly from the base scar to the apex. The ventral shoulder is very rounded.

*Dorsal edge*.—Shape — Somewhat similar to the ventral edge but tends to have a more cuneiform shoulder.

*Base scar*.—Shape — Considered round or oval and not considered particularly prominent.

*End view*.—Shape — Oval and somewhat plump.

*Pellicle*.—Color — Medium brown, and not particularly distinctive. The veins appear slightly darker and somewhat prominent, but the surface is smooth and not wrinkled.

*Surface texture*.—Has a light pubescence that is not particularly conspicuous.

*Double kernels*.—Numbers — Average, being approximately 12% of the sample reviewed.

*Flavor*.—Noteworthy.

*Quality*.—Good.

Although this new variety of almond tree possesses the described characteristics noted above, as a result of the growing conditions prevailing in the central part of the San Joaquin Valley of Central California, it is to be understood that variations of the usual magnitude and characteristics incident to changes in growing conditions, fertilization, pruning and pest control are to be expected.

Having thus described and illustrated my new variety of almond tree what I claim is new and desire to secure by plant Letters Patent is:

1. A new and distinct variety of almond tree substantially as illustrated and described, and which is somewhat similar to the Nonpareil almond tree (unpatented) but which is distinguished therefrom and characterized principally as to novelty by producing a nut which is ripe for harvesting and shipment approximately 8 days after the Nonpareil variety and approximately 6 to 7 days earlier than the Carmel almond tree (U.S. Plant Pat. No. 2641) at the same geographical location.

* * * * *

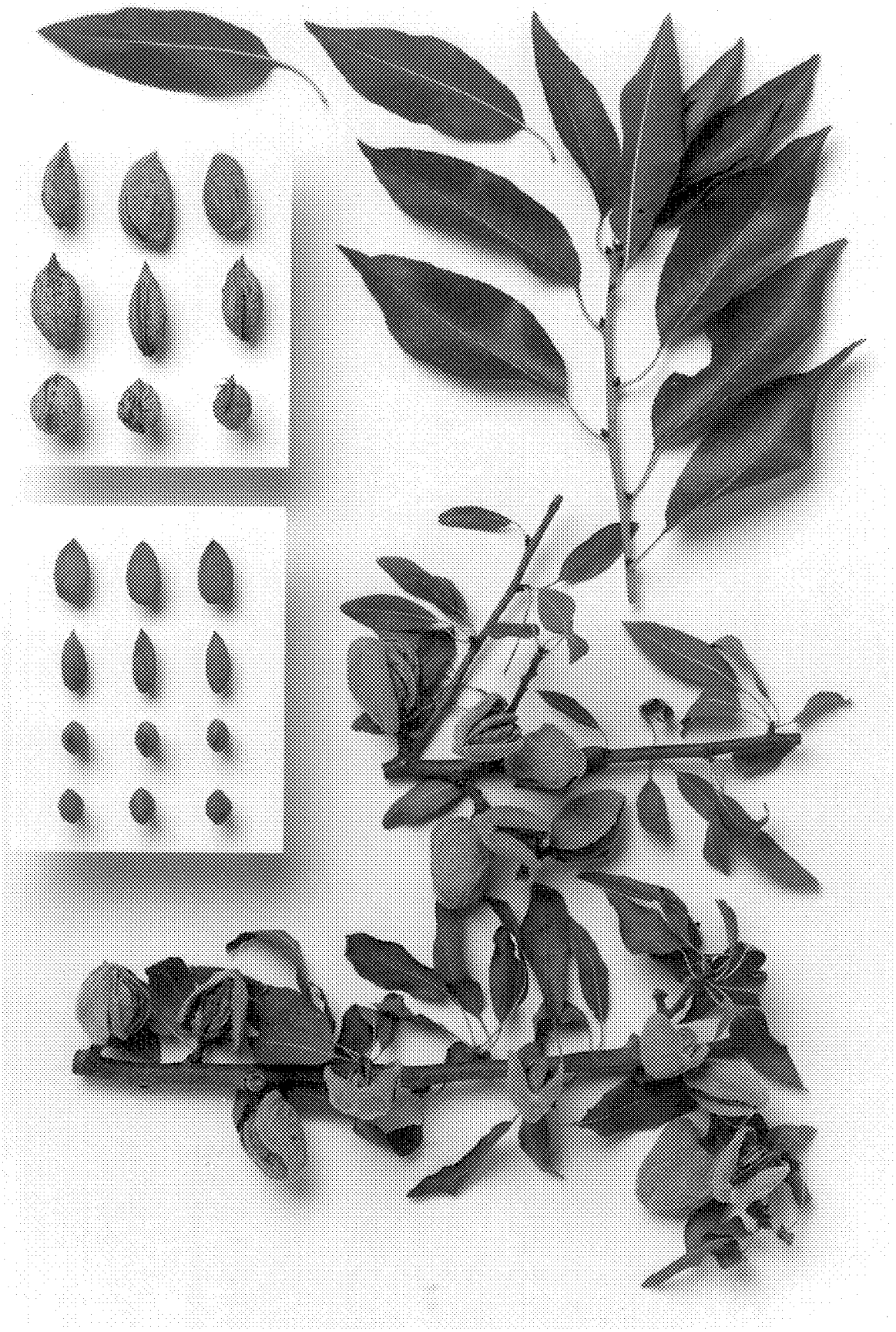

UNITED STATES PATENT AND TRADEMARK OFFICE

CERTIFICATE OF CORRECTION

PATENT NO. : Plant 11,096

DATED : October 19, 1999

INVENTOR(S) : Charles Mancebo

It is certified that error appears in the above-identified patent and that said Letters Patent is hereby corrected as shown below:

Col. 4, line 7
replace "leave"
with --leaves--.

Col. 6, line 13 After "Surface" insert -- Color --

Col. 6, line 21 After "Kernel." insert -- Shape --

Signed and Sealed this

Twentieth Day of June, 2000

*Attest:*

Q. TODD DICKINSON

*Attesting Officer*

*Director of Patents and Trademarks*